United States Patent [19]

Leigh

[11] Patent Number: 5,172,701
[45] Date of Patent: Dec. 22, 1992

[54] SINGLE USE AUTOMATED SOFT TISSUE ASPIRATION BIOPSY DEVICE

[75] Inventor: Harold G. Leigh, St. Louis County, Mo.

[73] Assignee: Medical Device Technologies, Inc., Gainesville, Fla.

[21] Appl. No.: 486,116

[22] Filed: Feb. 28, 1990

[51] Int. Cl.⁵ .............................................. A61B 10/00
[52] U.S. Cl. ................................... 128/753; 606/185; 128/752
[58] Field of Search ............... 128/751, 752, 753, 754; 606/185

[56] References Cited

U.S. PATENT DOCUMENTS

| | | |
|---|---|---|
| Re. 32,922 | 5/1989 | Levin et al. . |
| 1,835,122 | 12/1931 | Thevenot . |
| 2,360,051 | 10/1944 | Eweson . |
| 2,623,521 | 3/1951 | Shaw . |
| 2,881,756 | 4/1959 | Crosby et al. . |
| 3,088,454 | 5/1963 | Shute . |
| 3,477,423 | 11/1969 | Griffith . |
| 3,561,429 | 2/1971 | Jewett . |
| 3,587,560 | 6/1971 | Glassman . |
| 3,613,662 | 10/1971 | Chrysostomides . |
| 3,656,472 | 4/1972 | Moura . |
| 3,913,566 | 10/1975 | Lacey . |
| 3,989,033 | 11/1976 | Halpern et al. . |
| 3,995,619 | 12/1976 | Glatzer . |
| 4,177,797 | 12/1979 | Baylis et al. . |
| 4,239,040 | 12/1980 | Hosoya et al. . |
| 4,256,119 | 3/1981 | Gauthier . |
| 4,258,722 | 3/1981 | Sessions et al. . |
| 4,262,676 | 4/1981 | Jamshidi . |
| 4,266,555 | 5/1981 | Jamshidi . |
| 4,356,822 | 11/1982 | Altshuler . |
| 4,356,828 | 11/1982 | Jamshidi . |
| 4,403,617 | 9/1983 | Tretinyak . |
| 4,517,978 | 5/1985 | Levin et al. . |
| 4,600,014 | 7/1986 | Bersha . |
| 4,605,011 | 8/1986 | Naslund . |
| 4,619,272 | 10/1986 | Zambelli ............................. 128/753 |
| 4,641,663 | 2/1987 | Juhn . |
| 4,667,684 | 5/1987 | Leigh . |
| 4,699,154 | 10/1987 | Lindgren . |
| 4,747,414 | 5/1988 | Brossel ................................ 128/754 |
| 4,766,907 | 8/1988 | deGroot et al. ..................... 128/754 |
| 4,766,908 | 8/1988 | Clement . |
| 4,817,631 | 4/1989 | Schnepp-Pesch et al. ......... 128/753 |
| 4,919,146 | 4/1990 | Rhinehart et al. . |
| 4,986,278 | 1/1991 | Ravid et al. ........................ 128/753 |

FOREIGN PATENT DOCUMENTS 6154723  2/1974  U.S.S.R. .

OTHER PUBLICATIONS

Waters Instruments, Inc. (Johannah Medical Products)—2 pages.
The Jamshidi Soft-Tissue Biopsy Needle/Syringe—Catalog page.
The Jamshidi Muscle Biopsy Needle—Catalog No. MB-4008—Catalog page.
Gyneco, The Masterson Endometrial Biopsy Kit—Gyneco, Inc., 2 catalog pages.
"Radiology"—Oct. 1971—vol. 101, No. 1, p. 62., Birnbaum, M.D., et al.

Primary Examiner—William E. Kamm
Assistant Examiner—Kennedy J. Schaetzle
Attorney, Agent, or Firm—Emrich & Dithmar

[57] ABSTRACT

A biopsy device incorporating a housing, having a slide member therein, with one of a stylet or cannula connecting to the slide, while the other is fixed to the housing, such that when the slide member is shifted longitudinally within the housing, a displacement occurs between the forwardmost portions of the stylet and cannula, generating a reduced pressure therein, for aspirating a biopsy for analysis.

14 Claims, 3 Drawing Sheets

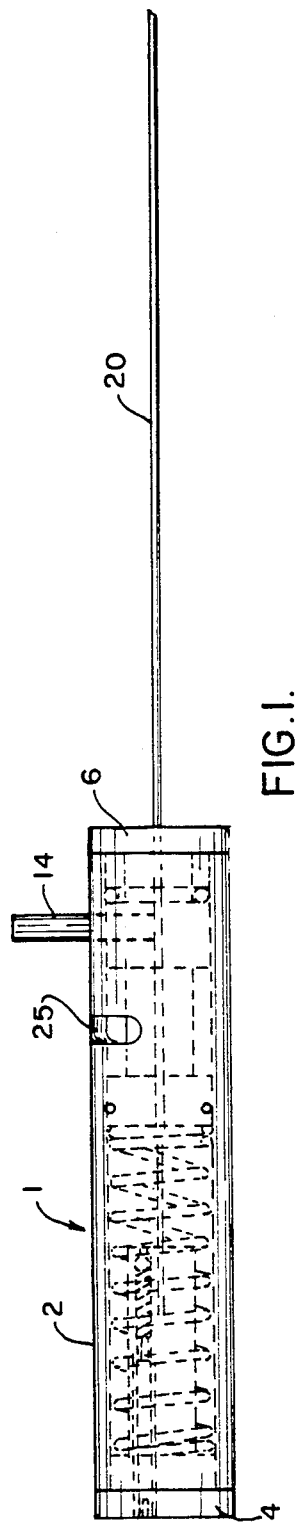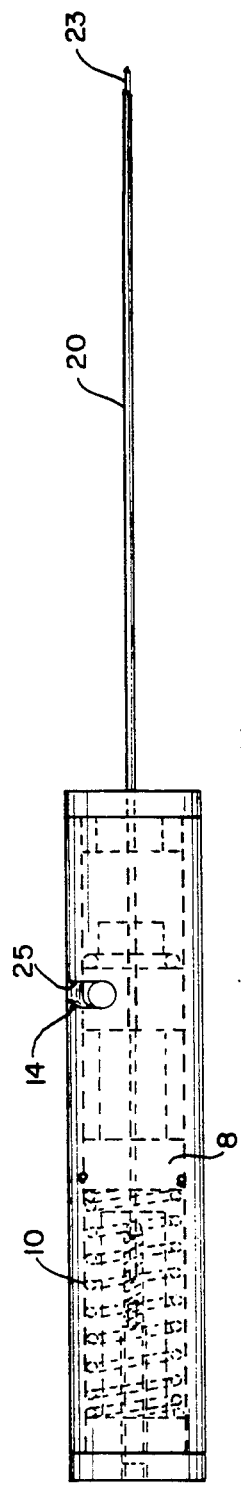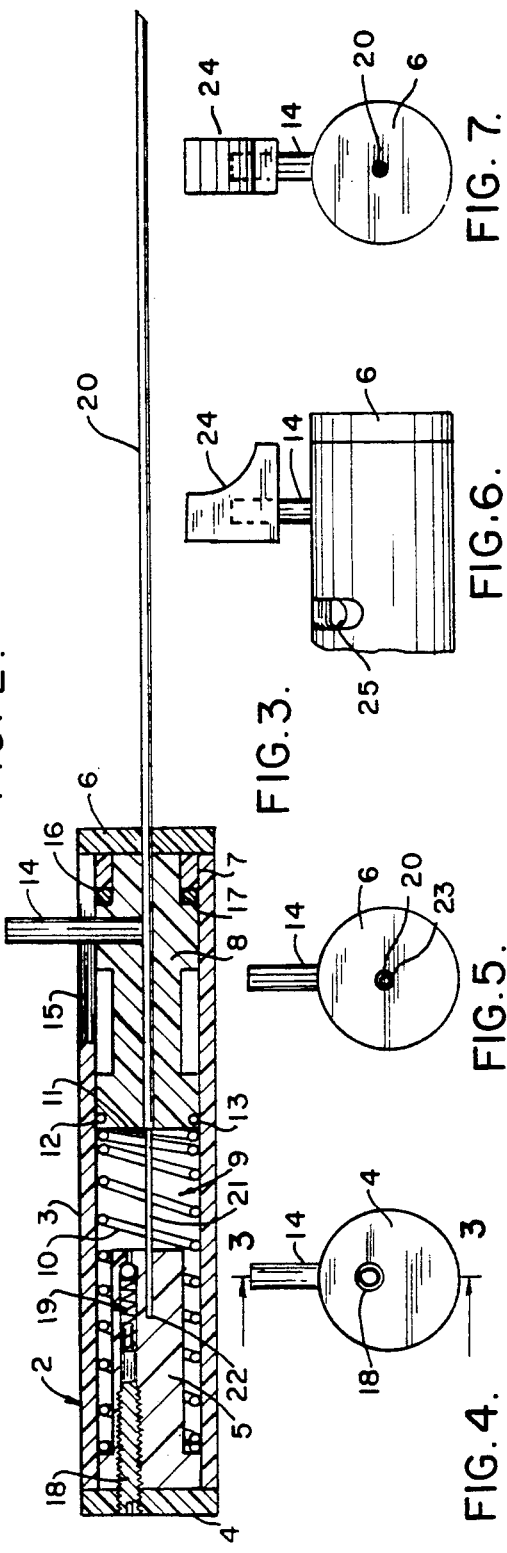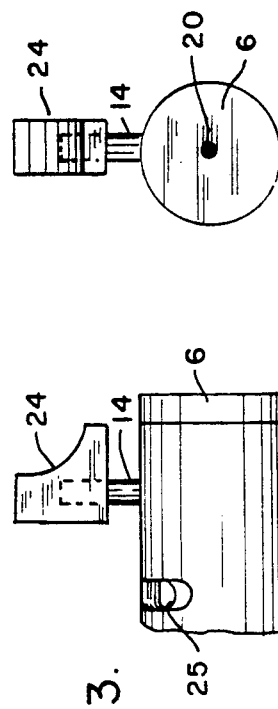

SINGLE USE AUTOMATED SOFT TISSUE ASPIRATION BIOPSY DEVICE

BACKGROUND OF THE INVENTION

This invention relates generally to a biopsy device, and more specifically, one that functions under the aspiration principle to obtain a biopsy specimen for medical analysis.

A variety of biopsy devices have long been available in the prior art. Most of these biopsy devices operate upon what might be identified as the "guillotine" principle, wherein a needle in combination with a cannuala is embedded into the vicinity of suspected tissue, and then the stylet is manipulated for reception of a segment of specimen into a recess provided proximate the stylet tip, at which time the cannula then is shifted into overriding relationship upon the stylet, and severs a small quantity of specimen, for retention within the stylet recess, for eventual removal and analysis. Thus, as can be readily understood, the biopsy specimen undertaken through the usage of the prior art type of apparatus actually collects, within a stylet recess, a potential specimen, and then severs a segment of it therefrom, for retention intermediate the cannula and the stylet, for removal and location onto a petri dish, or the like, for analysis.

An example of that type of conceptual use of mechanisms for obtaining a biopsy sample is shown in the earlier U.S. Pat. to Harold G. Leigh, No. 4,667,684, which discloses a hand held type of biopsy taking mechanism. But, as can be seen therein, the relationship between the stylet, with its arranged recess, and its manipulation into the cannula, during actuation, can be readily reviewed and understood.

Other types of prior art biopsy instruments, operating under the similar principle as that as the prior art device previously revealed, are shown in the U.S. Pat. to Griffin, No. 3,477,423. In addition, the United States patent to Radiplast A. B., as disclosed in U.S. Pat. No. 4,699,154, shows a related tissue sampling device. In addition, the U.S. Pat. No. 4,600,014, shows a transrectal prostate biopsy device and method.

The U.S. Pat. to Glatzer, No. 3,995,619, shows a combination subcutaneous suture remover, biopsy sampler and syringe. Basically, this device is utilized for the purpose of removing sutures previously emplaced within the body, or for taking of a biopsy, or which may be further used to permit subcutaneous introduction or extraction of fluids.

The patent to Halpern, U.S. Pat. No. 3,989,033, shows another form of surgical instrument for biopsies. Biopsies are obtained through its particularly configured cutting elements, within the structure, by the incision method. As can be seen, it explains that its cutting element makes a cut, in the guise of a rotary guillotine or knife, which cross sections the stretched portion of an organ being sampled.

The patent to Eweson, U.S. Pat. No. 2,360,051, shows a toilet device, which functions as a type of syringe incorporating vacuum means, for the purpose of removing skin surface blemishes.

The patent to Shaw, U.S. Pat. No. 2,623,521, shows an indicating stylet needle. This device is primarily used for making injections particularly in the spinal column. The relative displacement of the stylet and needle as shown herein are provided for the purpose of functioning as an indicator to let the doctor or nurse know when the inner end of the needle has passed through the tissue and enters an area containing gas or other fluid.

The patent to Shute, U.S. Pat. No. 3,088,454, shows another form of surgical instrument. This particular instrument is used for collecting cells for use as specimens for cytological diagnosis. This device does operate in the manner of a pipette obturator through manipulation of its thumb grip for moving its plunger rod rearwardly, in order to suck in cellular debris within the end portion of its cylinder 1.

The patent to Jewett, U.S. Pat. No. 3,561,429, shows another form of instrument for obtaining a biopsy specimen This device is formed in a gun configuration, having a triggerlike mechanism, which in a single stroke activates a vacuum producing means to draw a specimen into a tip supported by the gun, and then through the actions of its integral cutting edge, severes that drawn in specimen.

Finally, the patent to Gauthier, U.S. Pat. No. 4,256,119, shows a biopsy needle. This device is more concerned with a locking mechanism associated with its handle, but states that it does permit the attachment of a syringe to the needle body.

SUMMARY OF THE INVENTION

This invention contemplates the formation of a biopsy device, under a principle of operation that is distinct from what has been previously employed by those skilled in the art when designing apparatuses for this function, in that instead of cutting a sample of tissue during a biopsy taking treatment, the device of this current invention contains various components that function under the aspiration principle, for attracting a biopsy sample into a cannula, just forwardly of its stylet, during performance by the medical practitioner of obtaining a specimen for analysis from a suspected location of the patient.

More particularly, the concept of this invention is to develop a rapid and significant reduction in pressure within the cannula forwardmost tip, just in front of its stylet arranged therein, so that once the device, and more specifically the front of its cannula and stylet are arranged in proximity with the area to be sampled, and actuated, the rapid reduction in pressure generated due to a displacement between the cannula, and the stylet, at that location, aspirates a biopsy tissue into the cannula, for removal and analysis. Hence, whether the rapid reduction in pressure be generated just at the forwardmost tip of the cannula, or as in the preferred embodiment, is generated within a chamber within the device housing, by significantly reducing pressure down to an approximate vacuum, more or less, due to a rapid expansion in a chamber contained within its housing, this reduction in pressure is translated to the cannula forwardmost end, just in front of its stylet, in order to provide through suction of a specimen of tissue therein for biopsy analysis This can be achieved by a variety of methods, and manipulation of cooperating components, in a manner as will be subsequently reviewed.

More specifically, this invention is constructed incorporating a housing, generally fabricated of a tubular portion, and which functions as the means for containment of the operative components of the biopsy device therein, while simultaneously, affording a handle of some dimension that facilitates its grasp and manipulation by the practitioner, while initially setting or cocking of the device for actuation, while simultaneously providing a convenient handle for manipulation by the practitioner when inserting its associated stylet and needle into the vicinity of the suspected tissue, for actuating the device, and withdrawing it for obtaining that specimen tissue for analysis.

The tubular portion of the housing contains a hub at its back end, and connecting with the hub and fixed in position therewith, is the stylet of the apparatus. The stylet extends forwardly, through the front wall of the housing, and positions its tip at a fixed distance forwardly of the device. In addition, arranged within the housing, and between its hub, and its front wall, and provided for sliding movement therein is a slide means, which functions in the category of a piston, capable of shifting in two directions therein, one to provide for its rearward shift as when the device is being cocked for application. In addition, the slide means is capable of rapidly moving forwardly under accelerated conditions that provide for the generation of a reduction in pressure, of the type that effects the aspiration needed for generation of the reduced pressures required to achieve the results of the principle of operation of this development. Rearwardly of the slide means, within the housing, and in front of its hub is a formed volume varying chamber, and it is within this chamber that the significant reduction in pressure is generated, for translation to the forwardmost ends or tip of the cannula and stylet, for achieving that suction pressure required to facilitate the rapid drawing of a specimen into the cannula, at said location. A spring is provided within the chamber, supported by the hub, and biases against the rear end of the slide means, to provide for actuation of the device, in the manner as previously explained, to attain the desired aspiration results. To facilitate the generation of reduced pressure within the chamber, a seal means, in the form of an O-ring, is provided upon the slide means, and rides upon the inner surface of the housing tubular portion, so as to prevent release of pressure, or reduction in low pressure, once generated within the chamber, during actuation of the device.

The cannula of this development is fixedly mounted to the slide means, extends through the front wall of the housing, and is concentrically arranged around the stylet, in a manner as well known in the biopsy specimen obtaining art. Cocking means are provided upon the housing, in combination with the slide means, so that the slide means may be shifted rearwardly, and set into position for actuation of the device, against the bias of its spring, such that when a release of the device is made, once its cannula and stylet are implanted proximate the suspected tissue, the slide means is thrusted rapidly forwardly, under the bias of the located compressed spring, which creates the generation of a low pressure or suction within the volume of the expanding chamber, and such reduction in pressure is translated to the forwardmost tip within the cannula, by means of the slight clearance provided between the stylet and the interior of the cannula, so that the reduction in pressure generated at the tip, within the cannula, as the cannula is thrusted forwardly, while the stylet remains stationary, creates a rapid pressure decrease within that cannula tip, and creates a strong and instantaneous suction pressure for drawing a biopsy specimen therein, under the aspiration principle.

Other means are provided within this device, to facilitate its usage and application, such as the location of a one-way valve, within the housing, but preferably through its hub, so that as the device is cocked for usage, the increase in pressure generated as the slide means moves rearwardly within the housing, allows release and discharge of the developed pressure within the chamber, through the one-way valve, for its release exteriorly of the device. On the other hand, it is just as likely that that slight clearance provided between the cannula and the stylet, as the device is being cocked for usage, may allow for discharge of that generated pressure due to the contracting chamber size to allow resetting of the device to conveniently take place, without developed air pressure hindrance.

While the summary provided herein explains the features of this invention, and the desired attributes to be obtained from the principle of its operation, during actuation of this biopsy device, it must be recognized that the overall concept of this invention comprehends principally the generation of a low pressure within the forwardmost end or tip of the cannula, so that the suction pressure generated therein will attack and absorb a biopsy specimen, for immediate removal and analysis. For example, that reduction in pressure at the cannula tip may just as well be created and generated should the cannula itself be fixed to the housing, but that the stylet may be shifted rapidly rearwardly to a degree of displacement that generates a negative pressure within the cannula, at a magnitude that attracts a specimen of biopsy tissue therein, for eventual analysis. Normally, it is desired that the relationship between the stylet tip, and the forwardmost end of the cannula, be such that the stylet extends just a slight distance forwardly thereof, as the device is set for usage, so as to facilitate the piercing of the skin and insertion of the combination into the region of the suspected tissue, and from where the biopsy specimen is to be taken. Then, the object of the invention is to achieve a rapid reduction of pressure within the cannula at its forwardmost end, in order to aspirate a specimen of tissue therein. This can be achieved by a variety of methods, through the cooperative movement and action of the stylet and cannula, so that, even should the stylet be attached to the slide means, and be propelled rearwardly, rapidly, this action will generate a reduced pressure within the cannula tip, due to the reverse movement of the stylet therein, such as to attract a biopsy specimen therein. Obviously, under such conditions, a seal will be provided between the stylet, and the cannula, proximate their backend thereof, or between the slide means and housing, so that the increase in pressure that may develop within the chamber, behind the slide means, as the slide means moves in an opposite direction, reducing the size of the chamber, during actuation of the device, will allow for the discharge of generated pressure within the chamber to be released through the one-way valve, to exteriorly of the device. At the same time, the increase in the chamber size in front of the slide means and to the front of the housing, will develop a low pressure that translates to the front of the cannula, to attract a biopsy specimen therein. Thus, the increase in pressure, under such conditions, within the chamber, will have no effect upon the rapid reduction in pressure generated at the vicinity in front of the slide and at the forwardmost end of the cannula, due to the rapid rearward displacement of the stylet and its tip therein, as can be understood.

In attempting to analyze the principle of operation of this invention, empirically derived information affords the determination of formulation for determining the pressure generated through usage and application of this device. As previously explained, this device can be set or cocked for actuation by retracting its slide means, at least in the first and preferred embodiment, into a temporarily fixed condition, in preparation for its usage. The slide means is retracted against the bias of its spring, and cocked, at which time it is then inserted into the patient, and into the region or vicinity of the suspected tissue or organ. As explained, when such retraction has occurred, the forward tip of the stylet will extend just beyond the cutting edge of the cannula. Thus, under this condition, the combined stylet and cannula will facilitate their penetration of the skin, and the tissue, to the suspected region of the patient under analysis. The volumetric capacity of the chamber, within the housing, is reduced in volume as the slide means is shifted rearwardly, for cocking of the device, while at the same time compresses the dimensions of the biasing spring. Thus, the compression spring is set under significant compressive pressure in preparation for the actuation of the device, when operated. When the device is triggered, the cannula is quickly thrusted forwardly a short distance, while the stylet remains stationary, in the manner as previously summarized, at least in one embodiment. As this occurs, the lumen of the forwardmost portion of the cannula, in front of the stationary stylet, is filled with a core of severed tissue, which has been attracted into the cannula by means of aspiration negative pressure. However, it must be recognized that the distal end of this core sample yet may remain attached to body tissue or organ. In addition, that vacuum generated within the cannula, desirably then assists in fracturing of this attachment, as the assembly is withdrawn from the patient.

Also, when the device is actuated, the volume of the chamber suddenly becomes large, with respect to the cocked or set position of the slide means, and as a result, the expanding volume is created, for the chamber. This volume may be identified as $V_2$. Designating the reduced chamber volume, as when the device is cocked, as $V_1$, one can readily calculate the pressure reduction generated as the volume of the chamber of this device converts from $V_1$ to $V_2$, as the device is actuated. On the other hand, ambient atmosphere is prevented from attaining access into the chamber, under such condition, since the one-way valve prevents air from attaining access through the hub and into the housing, and likewise, due to the sealed relationship between the slide means, and the interior of the tubular portion of the housing, as previously reviewed. Thus, any reduction in pressure generated translates between the cannula and its internally arranged stylet, to the forwardmost portion of the cannula, where this suction pressure generated acts directly upon the surrounding tissue, since at this time the device will have been inserted into the patient in preparation for obtaining a specimen sample.

This relationship of the pressure, volume, mass and temperature of the gas, or reduction of pressure within the device, may be stated and analyzed by the equation PV=MRT.

P=Pressure
V=Volume
M=Mass
R=Gas Constant
T=Absolute Temperature

In the case of this invention, the mass of gas (as during expansion) remains constant, and therefore, M equals a constant. Since the gas, or reduced pressure generated within the chamber, is always the same, R also equals a constant. Any drop in temperature due to expansion (the Joule-Thompson effect) is, therefore, negligible, and hence, T equals a constant. Therefore, it can be readily determined that $PV$ equals a constant. Hence, $P_1V_1$ equals $P_2V_2$. It is readily known that $P_1$ equals 14.7 psi. $V_1$, calculated, for the preferred embodiment, may equal one ml. It is known, through calculation, that $V_2$ equals 10 ml. At least in the preferred embodiment. As a result, the formula generated for determining pressure conditions, or reduction in pressure generated, may be expressed as follows:

$$P_2 = \frac{P_1 V_1}{V_2} = \frac{14.7 \times 1}{10} = 1.47 \text{ psi absolute}$$

Thus, the pressure reduction in the preferred embodiment is almost ten to one, as calculated in the manner as explained herein.

It is, therefore, the principal object of this invention is to provide the structure of a biopsy device which operates under the principle of aspiration.

Still another object of this invention is to provide a biopsy device wherein a significantly reduced pressure is generated within the frontal lumen of its cannula, through manipulation and shifting of the operative components of the biopsy device of this invention.

Still another object of this invention is to provide the relative displacement between the cannula, and its stylet therein, so as to form a reduced pressure within the cannula for sucking a specimen of suspect tissue therein, for removal and eventual biopsy analysis.

Still another object of this invention is to provide mechanism, in the form of a convenient housing, having slide means therein, to provide relative displacement between a cannula, and stylet, to achieve aspiration for attraction of a biopsy specimen.

Still another object of this invention is to provide structural means that may provide for either movement or stationary retention of either a cannula, or its stylet, relative to each other, to produce rapid displacement between these components, for generating a negative pressure at the vicinity of the cannula forwardmost tip, for aspirating a specimen of tissue into the cannula lumen for retraction and analysis.

Another object of this invention is to provide a biopsy device that is disposable.

These and other objects will become more apparent to those skilled in the art upon reviewing the summary of the invention as made herein, and upon undertaking a study of the description of its preferred embodiment, in view of the drawings.

BRIEF DESCRIPTION OF THE DRAWINGS

In referring to the drawings, FIG. 1 discloses the biopsy device of this invention, in its static state;

FIG. 2 provides a view of the biopsy device of this invention in its set or cocked condition;

FIG. 3 provides a longitudinal cross sectional view of the biopsy device, in the condition as shown in FIG. 1;

FIG. 4 is a rear view thereof;

FIG. 5 is a front view thereof;

FIG. 6 is a partial view of the biopsy device disclosing finger gripping means attaching to its stem to facilitate its cocking in preparation for usage;

FIG. 7 is a front view of FIG. 6;

DESCRIPTION OF THE PREFERRED EMBODIMENT

Figure 8:
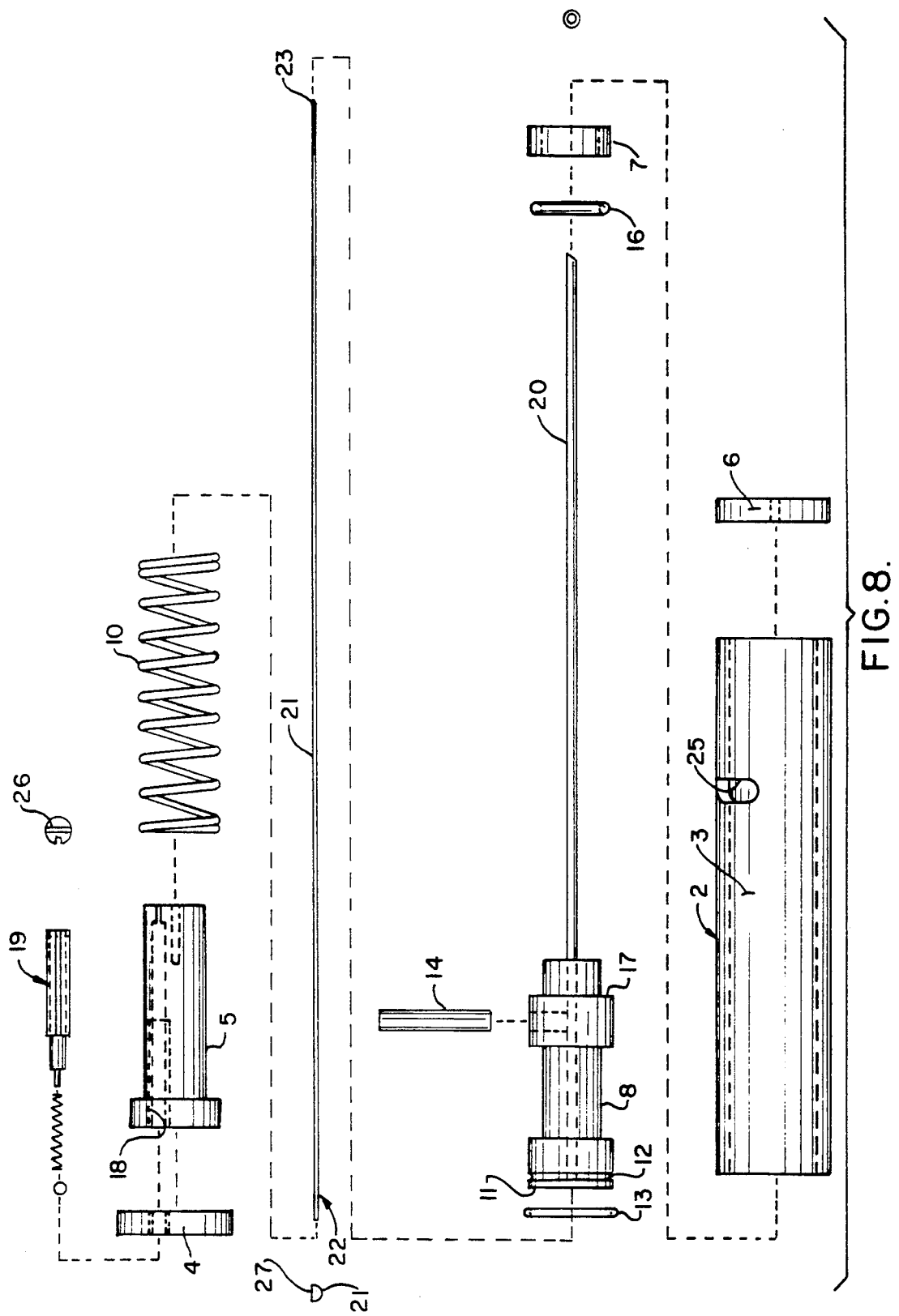
FIG. 8 is an exploded view of the various components, which when assembled, form the biopsy device of this invention.
Figure 9:
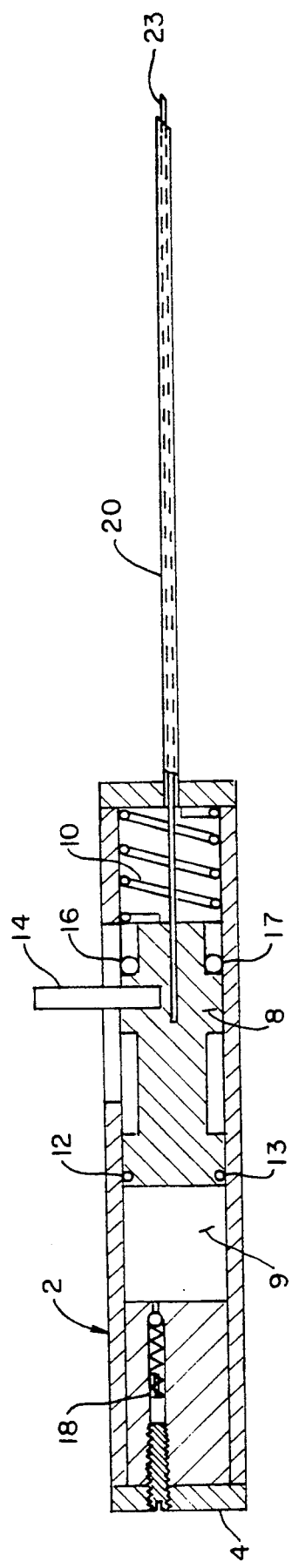
FIG. 9 is a view of a further embodiment of an aspiration biopsy device according to the present invention wherein the cannula is fixed to the housing and the stylet is movable with the slide member.

In referring to the drawings, and in particular FIG. 1, the biopsy device 1 of this invention is disclosed. It includes a housing 2 which is formed as a length of tubular portion 3, that extends the length of the housing, and is designed having convenient length and size so as to accommodate the operative components of this device therein, while simultaneously, furnishing ample physical characteristics to function as a convenient handle for facilitating usage of this device by the medical technician. See also FIG. 3. The back end of the housing is closed off by a back wall 4 and integrally connected to the back wall 4 is a hub 5, as noted.

The front of the housing 2 is closed by means of a front wall 6, and which connects with a sleeve 7 that extends interiorly of the housing 2, for purposes to be subsequently described.

Within the housing is provided a slide means 8, and the slide means is designed for sliding movement within the tubular portion 3, between a static state, as shown in FIGS. 1 and 3, or into a cocked position, as shown in FIG. 2.

Formed within the housing 2 is a chamber 9, and it is this chamber that varies in size and capacity and which furnishes the means for generation of a low or negative pressure as when this device is actuated during usage, as will be subsequently reviewed. Provided within the chamber 9 and mounted upon the hub 5 is a spring means 10, and which spring means biases against the back side 11 of the slide means 8, as can be seen.

The slide means 8 includes an annular groove therein, as at 12, and within the groove is provided a seal 13, formed of an O-ring, and which seals against the interior surface of the tubular housing 3, so as to provide a generally hermetic seal between the slide means, and the housing, during its shifting therein. In addition, some form of stem means 14 is fixed to the slide means 8, and extends exteriorly of the tubular portion 3 of the housing, projecting through its formed slot 15, as noted, and which is used for facilitating cocking of the device. Provided forwardly of the slide means 8, and resting against the sleeve 7 is a bumper 16 and which is provided for encountering the shoulder 17 as when the slide means reaches the forwardmost end of its stroke, during actuation of the device, so as to cushion the impact thereat.

Provided through the hub 5 is an aperture, as at 18, and located within the aperture, by means of its threaded engagement therein, is a one-way valve 19 as noted. Thus, as the slide means 8 is forced rearwardly, within the housing 2, by means of a drawback upon the stem means 14, the gas therein, as it begins to compress, will be allowed to bypass and be discharged from the housing, by means of the one-way valve 19, in a manner as can be readily understood. On the other hand, as the slide means 8 is thrusted forwardly, during actuation of the device, the negative pressure generated within the chamber 9, as it rapidly expands, will not have any air entering therein because of the presence of the one-way valve 19, as can be noted.

Further essential features of this invention include the cannula 20, which is fixed to the slide means 8. It has the stylet 21 arranged therethrough, with the back end of the stylet connecting to the hub 5, as at 22, while the front end of the stylet, as at 23, extends just slightly forwardly of the cannula, particularly when the device has been cocked, as shown in FIG. 2, in preparation for its application. On the other hand, as can be readily understood, as the slide means 8 is released, and projected forwardly, under a rapid thrust, the cannula overrides the stylet tip 23, moves rapidly forward for a fixed distance, to displace the stylet tip 23 within the cannula, an equivalent space inwardly of the cannula, so that a negative pressure is generated within the chamber 9, and is translated intermediate the cannula and stylet to the forward lumen of the cannula, to attract and absorb a specimen of the tissue therein, for biopsy analysis.

As can be seen in FIGS. 6 and 7, the stem 14 may include a finger grip 24 thereon, in order to facilitate the manipulation of the device, as when being cocked. When the device is being set for usage, it can be seen that the stem 14 is moved rearwardly, with respect to the housing, within the slot 15, until such time as it becomes aligned with the lateral slot 25, with the stem being moved into that lateral slot, to be retained in a cocked position in preparation for operation. Once cocked, the device will be in the position as shown in FIG. 2, with the sharp end of the stylet 23 slightly extending forwardly of the cannula 20, and can be conveniently inserted into the patient, in preparation for obtaining a specimen sample.

Thus, in operation, the device, and more specifically its stem 14, is shifted rearwardly, and arranged into the lateral slot 25, in the manner as shown in FIG. 2. As that occurs, the slide means 8 is shifted rearwardly, against the compression of the spring means 10, and is cocked into position. Thus, the chamber 9 has been substantially reduced to that of the spacing surrounding the hub 5, upon which the compression spring 10 sets, just rearwardly of the back wall 11 of the slide means 8. In this condition, as previously explained, the cannula and stylet will have the relationship as shown, particularly at their forward ends, as disclosed in FIG. 2, which facilitates their insertion into the patient, and into the suspected region from which a specimen is required. Once inserted, the stem 14 can be shifted laterally, into alignment with the housing slot 15, whereby the spring rapidly propels the slide means 8 forwardly, which allows the chamber 9 to rapidly expand, developing a substantial negative pressure therein, which pressure is translated to the forwardmost interior of the cannula 20, as it displaces forwardly a fixed distance from the stylet tip 23, which will now be located inwardly of the cannula, by a distance equivalent to that of the forward shift of the slide means 8, during the device's actuation. Hence, the negative pressure generated therein forms an aspiration activity within the cannula tip, which absorbs tissue therein, and which tissue comprises that specimen needed for biopsy analysis. At this time, the device 1 can be removed, is recocked, at which time the cannula moves rearwardly, with the slide means, as the stationary stylet forces the specimen tissue to become exposed at its forward end thereof. This specimen can then be placed onto a petri dish, or elsewhere, for analysis.

Other features of the invention can be seen upon further review of FIG. 8. For example, to facilitate the assembly of the one-way valve 19 into the hub channel 18, a slot 26 may be provided, for facilitating the usage of a screwdriver when threading said valve into position.

In addition, and in order to assure that any negative or reduced pressure developed within the chamber 9, as the device actuates, is translated to the forwardmost ends of the stylet and cannula, the stylet may have a planer configuration formed along its length, as indicated by the flattened condition as shown at 27, so adequate clearance is provided between the stylet, and the interior of the cannula, to assure that this pressure translation does occur. On the other hand, it is believed that there is yet adequate clearance between the stylet, as contained within the cannula, even without such formed planer configuration 27, that the negative pressure generated will be immediately transmitted to and pervade at the interior of the forwardmost portion of the cannula 20, during functioning of this device.

As previously summarized, the principle of this invention is to provide for the generation of a low or negative pressure, approximating a vacuum, instantaneously within the lumen of the forwardmost portion of the cannula 20, during actuation of this device. It can be achieved through the assembly and functioning of the structure as previously explained in the preferred embodiment. On the other hand, it is just as likely that the cannula may remain stationary, such as being fixed to the front wall 6 of the housing, while the stylet will be fixed to the slide means 8. And, the functioning of the slide means 8, and the spring 10, will be reversed, in that the spring will be located to the front of the slide means 8, and cocked in a forwardmost position, such that when released, the slide means 8 will rapidly accelerate rearwardly, under the bias of the replaced spring, to pull the stylet back, and thereby generate an instantaneous negative pressure within the lumen at the forwardmost portion of the cannula 20, to attract, by the aspiration principle, a specimen of tissue therein. Obviously, when that occurs, and since the back chamber 9 will be rapidly reducing in size when operating in that manner, instead of developing a negative pressure within the chamber 9, pressure will actually build up, but the one-way valve will allow that pressure to escape, and not effect the generation of a low pressure within the forwardmost lumen of the cannula 20. On the other hand, to make sure that none of the building pressure within the chamber 9 is translated intermediate the stylet and cannula to the front of this combination, as they are implanted within the suspect tissue, and which build-up of pressure would actually prevent the aspiration effect from taking place, it may be necessary to provide a seal either between the interior of the cannula 20, and the stylet 9, somewhere along their length, rearwardly of their front end, so as to prevent the built up pressure within the chamber 9, as the slide means 8 rapidly accelerates rearwardly, from being translated or transmitted to the front of the cannula, as previously explained. On the other hand, the seal 13 may suffice for this purpose, and the expanding chamber in front of the slide means 8 may develop adequate negative or low pressure that translates to the cannula tip. Thus, the rapid retraction of the stylet 21 within the cannula 20, under this alternative embodiment, will create a suction force within the forwardmost lumen of the cannula 20, attracting a specimen tissue therein, for biopsy analysis. This is just an example of how the aspiration principle of this invention may be employed with variations of structure, but yet to attain the same desirable results of this invention.

Variations or modifications to the subject matter of this invention as described herein may occur to those skilled in the art upon reviewing the subject matter of this disclosure. Such variations, if within the spirit of this invention, are intended to be encompassed within the scope of any claims to patent protection issuing upon this invention. The embodiments depicted herein are presented for illustrative purposes only.

Having thus described the invention what is claimed and desired to be secured by Letters Patent is:

1. A biopsy aspiration device comprising:
    a hollow cannula having a proximal end and a distal end;
    a stylet having a proximal end and a distal end and positioned within said cannula for axial movement relative thereto;
    a housing providing a sealed chamber and means for holding the operative components of the biopsy aspiration device;
    slide means movably associated with said housing in cooperative relationship with said sealed chamber, said slide means being movable from a cocked actuated position wherein the volume of said sealed chamber is minimized, to a released at rest position wherein the volume of said sealed chamber is maximized;
    biasing means engageable with said slide means when said slide means is in said cocked position to urge said slide means to said at rest position;
    cocking and releasing means associated with said slide means and said housing for moving said slide means against force of said biasing means to the cocked actuated position and for releasing said slide means to be moved to said released at rest position by said biasing means;
    said hollow cannula being communicated with said sealed chamber, and one of said stylet or said cannula having its proximal end fixedly anchored to said slide means and the other one of said stylet or said cannula having its proximal end anchored to said housing;
    whereby upon release of said slide means the resultant volume increase in said sealed chamber creates a pressure reduction, and the pressure reduction generated within said chamber is translated to the distal end of said cannula to effect aspiration of a biopsy specimen into the cannula during actuation of the device.

2. The device according to claim 1 wherein said stylet is fixed to said housing and said cannula is fixed to said slide means and movable therewith.

3. The device according to claim 1 wherein said cannula is fixed to said housing and said stylet is fixed to said slide means and movable therewith.

4. The device of claim 1 wherein said stylet has a contoured surface provided along its length to facilitate the translation of the pressure reduction from the chamber to the distal end of the stylet and cannula.

5. The device of claim 1 and including sealing means between the slide means and the housing to enhance the generation of pressure reduction within said chamber during actuation of the device when operated to obtain a biopsy specimen.

6. The device of claim 5 and including a buffer provided forwardly of said slide means within the housing to cushion the impact of the device during its actuation in obtaining a biopsy specimen.

7. The device of claim 1 and including a valve means provided through the housing to allow an escape of pressurized air from the chamber as the slide means is moved to its cocked actuated position in preparation for actuation in taking a biopsy specimen.

8. The device of claim 7 and wherein said valve means is a one way valve.

9. The device of claim 1 and wherein said cocking and releasing means comprises a stem, said stem connecting to said slide means and extending exteriorly of said housing, said stem capable of being manually manipulated for cocking of said biopsy device in preparation for its usage.

10. The device of claim 9 and wherein said housing has a slot therein furnishing clearance for the exterior extension of said stem for manual grasping and manipulation during cocking of the device.

11. The device of claim 10 and including sealing means provided between the slide means and the housing to enhance the generation of pressure reduction within said chamber for generating a pressure reduction during actuation of the device.

12. The device of claim 11 and wherein said sealing means comprises an O-ring arranged between the slide means and said housing.

13. The device of claim 11 and wherein said sealing means is arranged intermediate the location of the attachment of the stem to said slide means and the chamber.

14. A biopsy aspiration device comprising:
   a hollow cannula having a proximal end and a distal end;
   a stylet having a proximal end and a distal end and positioned within said cannula for axial movement relative thereto;
   a housing providing a sealed chamber and means for holding the operative components of the biopsy aspiration device;
   slide means movably associated with said housing in cooperative relationship with said sealed chamber, said slide means being movable from a cocked actuated position wherein the volume of said sealed chamber is minimized, to a released at rest position wherein the volume of said sealed chamber is maximized;
   biasing means engageable with said slide means when said slide means is in said cocked position to urge said slide means to said at rest position;
   cocking and releasing means associated with said slide means and said housing for moving said slide means against force of said biasing means to the cocked actuated position and for releasing said slide means to be moved to said released at rest position by said biasing means;
   said hollow cannula being communicated with said sealed chamber, said cannula having its proximal end fixedly anchored to said slide means and said stylet having its proximal end anchored to said housing;
   whereby upon release of said slide means the resultant volume increase in said sealed chamber creates a pressure reduction, and the pressure reduction generated within said chamber is translated to the distal end of said cannula to effect aspiration of a biopsy specimen into the cannula during actuation of the device.

* * * * *